United States Patent [19]

Mukouyama et al.

[11] Patent Number: 6,133,014

[45] Date of Patent: Oct. 17, 2000

[54] MALEATE ISOMERASE GENE

[75] Inventors: Masaharu Mukouyama; Shinzo Yasuda; Satomi Komatsuzaki, all of Ibaraki, Japan

[73] Assignee: Nippon Shokubai Co., Ltd., Osaka, Japan

[21] Appl. No.: 09/167,717

[22] Filed: Oct. 7, 1998

[30] Foreign Application Priority Data

Oct. 8, 1997 [JP] Japan ..................................... 9-276261

[51] Int. Cl.⁷ .............................. C12N 9/90; C12N 1/21; C12N 5/16; C12N 15/61; C07H 21/04
[52] U.S. Cl. ................ 435/233; 435/252.3; 435/252.33; 435/325; 435/320.1; 536/23.2
[58] Field of Search .................................. 435/233, 252.3, 435/252.33, 320.1, 325; 536/23.2

[56] References Cited

FOREIGN PATENT DOCUMENTS

| | | |
|---|---|---|
| 0747478 A1 | 11/1996 | European Pat. Off. . |
| 10004967 | 1/1998 | Japan . |
| 10033181 | 2/1998 | Japan . |
| 10066591 | 10/1998 | Japan . |
| WO9619571 | 6/1996 | WIPO . |

OTHER PUBLICATIONS

Hatakeyama et al. (Oct. 9, 1997) BBRC, vol. 239, pp. 74–79.

GenBank accession R98389 (Feb. 17, 1997).

*Primary Examiner*—Elizabeth Slobodyansky
*Attorney, Agent, or Firm*—Foley & Lardner

[57] ABSTRACT

The present invention provides a gene coding for maleate isomerase excellent in stability, a recombinant vector having the gene, and a transformant transformed with the recombinant vector. According to the present invention, maleate isomerase excellent in stability can be produced efficiently in a large amount.

5 Claims, No Drawings ically for production is long. NSM-4 has already been applied for a patent (Japanese Patent Application No. 155833/1996).

MALEATE ISOMERASE GENE

FIELD OF THE INVENTION

The present invention relates to a gene coding for maleate isomerase, recombinant DNA containing the gene, a transformant carrying the recombinant DNA and a process for producing maleate isomerase by use of the transformant.

BACKGROUND OF THE INVENTION

Microorganisms belonging to the genera Alcaligenes, Pseudomonas, Achromobacter, Aerobacter, Bacillus and Brevibacterium are known as microorganisms producing L-aspartic acid from maleic acid and ammonia, and some of them have already been applied for patents (Japanese Patent Publication Nos. 2793/1963, 11993/1967, 11994/1967, and 8710/1968).

Two kinds of enzyme, that is, maleate isomerase and aspartase, are involved in conversion of ammonium maleate into L-aspartic acid, where aspartase is relatively stable, while maleate isomerase is unstable and its activity is inherently liable to reduction in particular by oxygen.

Further, the stability of this maleate isomerase varies depending on the strain, and if the microorganism is immobilized for use, the half-life of the activity is short and satisfactory production is not attained under the present circumstances.

SUMMARY OF THE INVENTION

The object of the present invention is to provide a gene for maleate isomerase excellent in stability, a recombinant vector containing the gene, and a transformant transformed with the recombinant DNA.

That is, the present invention relates to DNA encoding a protein of (a) or (b) follows:

(a) a protein whose amino acid sequence is represented by SEQ ID NO:1 or 2; and (b) a protein derived from the protein of (a) by substitution, deletion or addition of amino acid in the amino acid sequence defined in (a) and having maleate isomerase activity.

As a specific example of the DNA, mention is made of e.g. DNAs shown in SEQ ID NOS:3 and 4. Deleted, substituted or added amino acids in (b) above refer preferably to one or several amino acids although the number of such amino acids is not particularly limited insofar as the protein has maleate isomerase activity.

Further, the present invention relates to a recombinant vector containing either of the above DNAS.

Further, the present invention relates to a transformant transformed with the recombinant vector.

Further, the present invention relates to a process for producing maleate isomerase, which comprises culturing the transformant in a medium and recovering maleate isomerase from the culture.

The addition, deletion or substitution of amino acids as described above can be effected by site-directed mutagenesis known in the art (see e.g. Nucleic Acid Research, Vol. 10, No. 20, pp. 6487–6500), and one or several amino acids are amino acids which can be added, deleted or substituted by site-directed mutagenesis.

DETAILED DESCRIPTION OF THE INVENTION

Hereinafter, the present invention is described in detail.

The microorganism used for preparing the gene of the present invention may be any microorganism producing maleate isomerase, and preferable examples are Citrobacter amalonaticus or Pseudomonas fluorescens, more preferably Citrobacter amalonaticus NSM-10 (FERM BP-6541) or Pseudomonas fluorescens NSM-4 (FERM BP-6037). The characterizing features of these 2 strains are that they produce maleate isomerase excellent in stability while the activity half-life for production is long. NSM-4 has already been applied for a patent (Japanese Patent Application No. 155833/1996).

First, genomic DNA is isolated from the microorganism. Isolation of genomic DNA can be conducted using a method known in the art, such as the SDS method, lysozyme-SDS method, or CTAB method. Preferably, the lysozyme-SDS method is used.

Then, the genomic DNA is cleaved in a usual manner with suitable restriction enzymes, and the resulting DNA is ligated to a known vector to prepare a recombinant DNA molecule. For cloning, a host microorganism is transformed with the DNA molecule. The vector includes but is not limited to pUC18. The host microorganism may be any microorganism in which the integrated gene can be maintained stably. By way of example, DH10B can be mentioned as a strain of E. coli. The method of transforming the host microorganism with the recombinant DNA molecule can be any method known in the art. For example, in vitro packaging can be used.

Then, the recombinant microorganisms obtained in this manner are screened for those containing the maleate isomerase gene. This screening can be carried out by culturing the recombinant microorganisms in a suitable medium and then measuring the enzyme activity of isomerizing maleic acid.

The recombinant DNA molecule is extracted from the recombinant microorganism thus selected. This extraction can be conducted using any conventional method for preparation of plasmid or phage DNA. A cleavage pattern of this recombinant DNA molecule by various restriction enzymes is analyzed by electrophoresis or the like.

The recombinant DNA molecule is then cleaved with various restriction enzymes, and its fragments hybridizing with a probe for detecting the maleate isomerase gene are detected. The detection probe is prepared by labeling several kinds of DNA oligomer synthesized on the basis of codons corresponding to an N-terminal amino acid sequence or a middle amino acid sequence determined by analyzing maleate isomerase in a usual manner. The DNA oligomers can be synthesized according to a method known in the art. The label used therein may be any conventional label, preferably Fluorescein-b 11.dUTP.

From the detected fragments, a suitable fragment is selected and ligated to a vector to construct a recombinant vector. It is used to transform a microorganism to give a transformant.

The procedures of preparing this transformant are not limited to those described above. For example, the genomic DNA is isolated as described above, and its fragments obtained by digestion with various restriction enzymes are analyzed by Southern hybridization with the above DNA probe, and a vector containing the fragment thus selected is used to transform a suitable host. The transformant thus obtained is cultured in a suitable medium, and the transformant having the ability to produce maleate isomerase can be selected by measuring maleate isomerase activity.

This transformant is a strain carrying the DNA of the present invention to produce maleate isomerase efficiently.

After this strain is cultured, its plasmid is extracted. An example of the microorganism is E. coli. To extract the plasmid, conventional methods can be used. The nucleotide sequence of the insert in the plasmid is analyzed, and on the basis of its sequence, the sequence of the whole maleate isomerase region in the above-described recombinant DNA molecule is determined.

The 2 DNAs of the present invention can be amplified by PCR using genomic DNA from the deposited microorganisms described above. The DNA can be amplified by PCR where an oligonucleotide consisting of about 20 nucleotides upstream from the gene obtained above and an oligonucleotide complementary to about 20 nucleotides downstream from the gene are used as primers and the genomic DNA is used as a template. In particular, the following prier sets can be used for amplifying the maleate isomerase gene of Citrobacter amalonaticus NSM-10 or Pseudomonas fluorescens NSM-4 as described above.

Citrobacter amalonaticus NSM-10

Forward side: 5'-ATGAAAAGTTTTCGAATCGGCCA AATCGTTCCCAGCTCC-3' (SEQ ID NO:5)

Reverse side: 5'-TTAGTAAGCGCCCGAGAGGAGAT GGCCCGG-3' (SEQ ID NO:6)

Pseudomonas fluorescens NSM-4

Forward side: 5'-ATGACCAAGCCCTACCGTATCGG CCAGATCGTGC-3' (SEQ ID NO:7)

Reverse side: 5'-TCAGTAGGCGCCCGACAGCAAG GCGCC-3' (SEQ ID NO:8)

EXAMPLES

Hereinafter, the present invention is described in detail with reference to the Examples, which however are not intended to limit the scope of the present invention.

Example 1

(1) Isolation and Cloning of Genomic DNA

Total DNA was isolated from a maleate isomerase-producing microorganism Pseudomonas fluorescens NMS-4. Isolation of the DNA was conducted using a modification of the method of Marmur et at. (J. Mol. Biol., 3, 208 (1961)) used for Pseudomonas. Pseudomonas fluorescens NSM-4 was cultured overnight in LB medium, and the microorganism was recovered from the culture by centrifugation. It was lyzed with lysozyme and SDS, extracted with phenol, and precipitated with ethanol to separate the total DNA.

The total DNA thus separated was cleaved with restriction enzyme Sau3AI for a suitable time and fragments in the range of 3000 to 9000 base pairs were recovered by agarose gel electrophoresis. The recovered Sau3AI-treated fragments were cloned into a BamHI site in the known vector pUC18. E. coli DH108B was transformed in a usual manner with this vector to prepare a gene library of Pseudomonas fluorescens NSM-4. As the library, an ampicillin-resistant transformant was obtained.

(2) Selection of Transformant

The ampicillin-resistant transformant was selected by measuring its enzyme activity of isomerizing maleic acid. The ampicillin-resistant transformant was inoculated via a loop of platinum into 3 ml maleic acid medium (Table 1) containing 100 γ ampicillin and cultured overnight, and the microorganism was recovered by centrifuging 1.5 ml of the culture. The recovered microorganism was suspended in 1 ml of 20% maleic acid substrate solution (Table 2) and reacted at 30° C. overnight. This substrate solution contained aspartase prepared from E. coli so that fumaric acid formed by isomerization of maleic acid was converted into L-aspartic acid. After reaction, a part of the reaction solution was diluted 400-fold with distilled water and measured for its formed L-aspartic acid by HPLC analysis under the following conditions.

Column: Capsule Pack C18 UG120S-5 (Shiseido Co., Ltd.)
Temperature: 40° C.
Eluent: 30 mM $NH_4H_2PO_4$ (pH 2.5)
Flow rate: 1 ml/min
Detector: UV (210 nm)

TABLE 1

Composition of the maleic acid medium

| | |
|---|---|
| Maleic acid | 10 g |
| $(NH_4)_2SO_4$ | 5 g |
| $KH_2PO_4$ | 1 g |
| $K_2HPO_4$ | 3 g |
| $MgSO_4 \cdot 7H_2O$ | 0.5 g |
| Yeast extract | 20 g |
| NaOH | 5.5 g |
| 1 L distilled water, pH 6.2, autoclaved at 121° C. for 15 minutes | |

TABLE 2

Composition of the maleic acid substrate solution

| | |
|---|---|
| maleic acid | 200 g |
| magnesium sulfate | 0.5 g |
| 1 L adjusted with ammonia water to pH 8.3 | |

The substrate solution was prepared by adding 1 ml Triton X-100 and 2000 U aspartase from E. coli to the above solution.

When about 2000 transformants were subjected to the above-described reaction, one transformant formed L-aspartic acid. The plasmid was recovered from this transformant by the alkali-SDS method and then treated with various restriction enzymes, and the DNA fragments were analyzed by agarose gel electrophoresis. As a result, it was found that the DNA insert in the plasmid was 5.6 kb-long and was cleaved at one site cleaved with SacI or XbaI, at two sites with KpnI or NcoI, and at three sites with SmaI or SphI, but not cleaved with BamHI, HindIII or EcoRI. This plasmid was designated pMI503.

(3) Preparation of DNA Probe

The N-terminal amino acid sequence of maleate isomerase from Pseudomonas fluorescens NSM-4 was analyzed by a protein sequencer (447A, Applied Biosystems). As a result, the following amino acid sequence was obtained as the N-terminal:

Met Thr Lys Pro Tyr Arg Ile Gly Gln Ile Val Pro Ser Ser Asn Thr Thr Met Glu Thr Glu (SEQ ID NO:9)

On the basis of codons corresponding to its partial sequence, that is, Val Pro Ser Ser Asn Thr Thr Met Glu Thr Glu (SEQ ID NO:10), 12 kinds of DNA oligomer consisting of the following 32 nucleotides were synthesized by the phosphoroamidite method: 5'-GTICCIAGCTCIAACACIACIATGGAAACIGA-3' (SEQ ID NO:11). Here, I is inosine (corresponding to an arbitrary nucleotide), R is purine base A or G, and Y is pyrimidine base C or T. In CIATGG in this sequence, the presence of a NcoI restriction site was estimated. This synthetic DNA oligomer was labeled with Fluorescein-11.dUTP by terminal deoxynucleotidyl transferase and used as a detection probe for the maleate isomerase gene.

(4) Southern Hybridization

The above-described DNA fragments cleaved with the restriction enzymes and NcoI were separated by agarose gel electrophoresis, transferred to a nylon membrane and subjected to Southern hybridization with the previously prepared detection probe to examine whether fragments hybridizing therewith were present or not.

As a result, a 4-kb fragment cleaved with KpnI, a 1.4-kb fragment with SmaI, a 3-kb fragment with SphI, a 2.6-kb fragment with NcoI, and a 4.1-kb fragment with XbaI hybridized with the probe.

(5) Cloning

Out of the fragments obtained in item (4) above, the 2.6-kb fragment cleaved with NcoI was blunt-ended with DNA Blunting Kit (Takara Shuzo Co., Ltd.) and subcloned in a SmaI site in pUC18.

E. coli was transformed with the resulting plasmid and cultured, and the plasmid was extract from the E. coli by the alkali-SDS method. This plasmid was designated pPM503. The DNA nucleotide sequence of the insert in this plasmid was analyzed by the dideoxy method, and as a result, the following nucleotide sequence corresponding to the N-terminal amino acid sequence of maleate isomerase was found:

5'-ATGACCAAGCCTACCGTATCGGCCAGATCGTG CCGAGTTCGAACACCACCA-3' (SEQ ID NO:12)

On the basis of this sequence, a primer for next sequencing was prepared, and analysis of 250 bases in each sequencing was repeatedly performed. By performing analysis 4 times, the sequence of the whole maleate isomerase region in plasmid pMI503 was determined.

(6) Expression of the Maleate Isomerase Gene in E. coli

E. coli having the above-described pMI503 plasmid and E. coli having pUC18 plasmid were inoculated respectively via a loop of platinum into 5 ml medium shown in Table 1 and cultured at 37° C. overnight under shaking. The microorganism was recovered by centrifuging 1.5 ml of the culture and then suspended in 0.5 ml maleic acid substrate solution shown in Table 2 to conduct the conversion reaction of maleic acid at 30° C. By adding aspartase prepared from E. coli to the substrate solution, the formed fumaric acid was detected as L-aspartic acid. This analysis was conducted according to item (2) above. By the 16-hour reaction, E. coli DH10B-503 having pMI503 plasmid indicated 90% conversion of maleic acid, while DH108 having pUC18 plasmid not containing the insert indicated 0% conversion.

Example 2

(1) Preparation of DNA Probe

The N-terminal amino acid sequence of maleate isomerase from a maleate isomerase-producing microorganism Citrobacter amalonaticus NSM-10 was analyzed by a protein sequencer (477A, Applied Biosystems). As a result, the following amino acid sequence was obtained as the N-terminal structure:

Met Lys Ser Phe Arg Ile Gly Gln Ile Val Pro Ser Ser Asn Thr Thr Met Glu Thr Glu (SEQ ID NO:13).

On the basis of codons corresponding to its partial sequence, that is, Val Pro Ser Ser Asn Thr Thr Met Glu Thr Glu (SEQ ID NO:10), 12 kinds of DNA oligomer consisting of the following 32 nucleotides were synthesized by the phosphoroamidite method:
5'-GTICCIAGCTCIAACACIACIATGGAAACIGA-3' (SEQ ID NO:11). Here, I is inosine (corresponding to an arbitrary nucleotide), R is purine base A or G, and Y is pyrimidine base C or T. This synthetic DNA oligomer was labeled with Fluorescein-11.dUTP by terminal deoxynucleotidyl transferase and used as a detection probe for the maleate isomerase gene.

(2) Isolation of Genomic DNA

Total DNA was isolated from the maleate isomerase-producing microorganism Citrobacter amalonaticus NSM-10. Isolation of the DNA was conducted using a modification of the method of Marmur et at. (J. Mol. Biol., 3, 208 (1961)) used for Pseudomonas. Citrobacter amalonaticus NSM-10 was cultured overnight in LB medium, and the microorganism was recovered from the culture by centrifugation. It was lyzed with lysozyme and SDS, extracted with phenol, and precipitated with ethanol to separate the total DNA.

(3) Southern Hybridization

The separated total DNA was cleaved with restriction enzymes BamHI, EcoRI, SacI, KpnI, SmaI, XbaI, SalI, PstI and HindIII and the fragments were separated by agarose gel electrophoresis. The separated fragments were transferred from the agarose gel to a positively charged nylon membrane.

Blots having the DNA fragments transferred thereto were subjected to Southern hybridization with the previously prepared detection probe to examine hybridizing fragments. As a result, it was found that a restriction enzyme PstI-cleaved 1.2 kbp fragment from the total DNA of Citrobacter amalonaticus NSM-10 hybridized strongly with the probe.

(4) Cloning

The restriction enzyme PstI-cleaved 1.2 kbp fragment from the total DNA of Citrobacter amalonaticus NSM-10 was separated by electrophoresis, recovered from the agarose gel and cloned into a PstI site in the known vector pUC18. E. coli DH108B was transformed in a usual manner with this vector to prepare a gene library of Citrobacter amalonaticus NSM-10. As the library, an ampicillin-resistant transformant was obtained.

(5) Selection of the Transformant

The ampicillin-resistant transformant was selected by measuring its enzyme activity of isomerizing maleic acid. The ampicillin-resistant transformant was inoculated via a loop of platinum into 3 ml maleic acid medium (Table 1) containing 100 γ ampicillin and cultured overnight, and the microorganism was recovered by centrifuging 1.5 ml of the culture. The recovered microorganism was suspended in 1 ml of 20% maleic acid substrate solution (Table 2) and reacted at 30° C. overnight. This substrate solution contained aspartase prepared from E. coli so that fumaric acid formed by isomerization of maleic acid was converted into L-aspartic acid. After overnight reaction, a part of the reaction solution was diluted 400-fold with distilled water and measured for its formed L-aspartic acid by HPLC analysis. The conditions for HPLC analysis were as described in item (2) in Example 1.

After 10 transformants were reacted, 6 transformants formed L-aspartic acid. The plasmid was recovered from one of these transformants and designated pMI10a.

The DNA nucleotide sequence of the insert in this plasmid was analyzed by the dideoxy method, and as a result, the following nucleotide sequence corresponding to the N-terminal amino acid sequence of maleate isomerase was found:

5'-ATGAAAAGTTTTCGAATCGGCCAAATCGTTCC CAGCTCCAATACTACAATGGAGACAGAA-3' (SEQ ID NO:14)

And this insert was found to contain the whole region of the 750-bp maleate isomerase gene coding for 250 amino acids.

(6) Expression of the Maleate Isomerase Gene in E. coli

E coli having the above pMI10a plasmid and E. coli having pUC18 plasmid were inoculated respectively via a loop of platinum into 5 ml medium shown in Table 1 and cultured at 37° C. overnight under shaking. The microorganism was recovered by centrifuging 1.5 ml of the culture and then suspended in 0.5 ml maleic acid substrate solution shown in Table 2 to conduct the conversion reaction of maleic acid at 30° C. By adding aspartase prepared from *E. coli* to the substrate solution, the formed fumaric acid was detected as L-aspartic acid. This analysis was conducted according to item (5) above. By the 16-hour reaction, *E. coli* DH10B-10a having plasmid pMI110a indicated 95% conversion of maleic acid, while DH10B having insert-free plasmid pUC18 indicated 0% conversion.

According to the present invention, there can be obtained a gene coding for maleate isomerase, recombinant DNA containing the gene, and a transformant carrying the recombinant DNA. Maleate isomerase can be efficiently produced by use of said transformant.

What is claimed is:

1. DNA encoding a protein of (a) or (b) as follows:
   (a) a protein whose amino acid sequence is represented by SEQ ID NO:1 or 2; and (b) a protein having a sequence according to SEQ ID NO:1 or 2 in which there is a single amino acid substitution, deletion or addition, wherein said protein (b) has maleate isomerase activity.

2. DNA according to claim 1 wherein the DNA is a nucleotide sequence shown in SEQ ID NO:3 or 4.

3. A recombinant vector containing the DNA described in claim 1.

4. A transformant transformed with the recombinant vector described in claim 3.

5. A process for producing maleate isomerase, which comprises culturing the transformant described in claim 4 in a medium and recovering maleate isomerase from the culture.

* * * * *

SEQUENCE LISTING

```
<160> NUMBER OF SEQ ID NOS: 14

<210> SEQ ID NO 1
<211> LENGTH: 250
<212> TYPE: PRT
<213> ORGANISM: Pseudomonas fluorescens

<400> SEQUENCE: 1

Met Thr Lys Pro Tyr Arg Ile Gly Gln Ile Val Pro Ser Ser Asn Thr
 1               5                  10                  15

Thr Met Glu Thr Glu Ile Pro Ala Met Leu Leu Ala Arg Gln Ala Ile
                20                  25                  30

Arg Pro Glu Arg Phe Thr Phe His Ser Ser Arg Met Arg Met Lys Gln
            35                  40                  45

Val Lys Lys Glu Glu Leu Ala Ala Met Asp Gly Glu Ser Asp Arg Cys
    50                  55                  60

Ala Val Glu Leu Ser Asp Ala Lys Val Asp Val Leu Gly Tyr Ala Cys
65                  70                  75                  80

Leu Val Ala Ile Met Ala Met Gly Leu Gly Tyr His Arg Gln Ser Glu
                85                  90                  95

Lys Arg Leu Gln Lys Ala Thr Ala Asp Asn Asp Ala Leu Ala Pro Val
            100                 105                 110

Ile Thr Ser Ala Gly Ala Leu Val Glu Ala Leu His Val Met Lys Ala
        115                 120                 125

Lys Arg Ile Ala Ile Val Ala Pro Tyr Met Lys Pro Leu Thr Glu Leu
    130                 135                 140

Val Val Asn Tyr Ile Arg Glu Glu Gly Phe Glu Val Gln Asp Trp Arg
145                 150                 155                 160

Ala Leu Glu Ile Pro Asp Asn Leu Ala Val Ala Arg His Asp Thr Ala
                165                 170                 175

Asn Leu Pro Gly Ile Val Ala Gly Met Asn Leu Glu Gly Val Asp Val
            180                 185                 190

Val Val Leu Ser Ala Cys Val Gln Met Gln Ser Leu Pro Ala Val Ala
        195                 200                 205

Lys Val Glu Ala Gln Thr Gly Lys Pro Val Val Thr Ala Ala Ile Ala
    210                 215                 220

Thr Thr Tyr Ala Met Leu Lys Ala Leu Asp Leu Glu Pro Val Val Pro
225                 230                 235                 240

Gly Ala Gly Ala Leu Leu Ser Gly Ala Tyr
                245                 250

<210> SEQ ID NO 2
<211> LENGTH: 250
<212> TYPE: PRT
<213> ORGANISM: Citrobacter amalonaticus

<400> SEQUENCE: 2
```

```
Met Lys Ser Phe Arg Ile Gly Gln Ile Val Pro Ser Ser Asn Thr Thr
1               5                   10                  15

Met Glu Thr Glu Ile Pro Ala Met Leu Thr Ser Arg Tyr Ser Met Tyr
            20                  25                  30

Pro Asp Glu Gln Phe Thr Phe His Ser Ser Arg Met Arg Met Met His
                35                  40                  45

Val Ser Pro Glu Glu Leu Lys Lys Met Asp Ile Asp Ser Asp Arg Cys
    50                  55                  60

Ala Leu Glu Leu Ser Asp Ala Arg Val Asp Val Met Ala Tyr Ala Cys
65                  70                  75                  80

Leu Val Ala Ile Met Cys Gln Gly Ala Gly Tyr His Lys Val Ser Gln
                85                  90                  95

Glu Arg Leu Gly Lys Ala Val Ala Ser Asn Asn Ser Ser Ser Pro Val
                100                 105                 110

Leu Ser Ser Ala Gly Ala Leu Ile Asp Ser Leu Ala Met Leu Glu Tyr
                115                 120                 125

Lys Lys Ile Ser Ile Ile Thr Pro Tyr Met Lys Pro Leu Thr Gln Gln
            130                 135                 140

Val Ile Asp Tyr Ile Glu Ala Ala Gly Ile Glu Val Val Asp Ser Ile
145                 150                 155                 160

Ser Leu Glu Val Ser Asp Asn Leu Glu Val Gly Arg Leu Asp Pro Met
                165                 170                 175

Asn Leu Val Gly His Ala Asp Lys Leu Lys Ile Gly Gln Ala Asp Gly
                180                 185                 190

Val Val Leu Ser Cys Cys Val Gln Met Pro Ser Leu Pro Ala Ile His
                195                 200                 205

Leu Val Gln Asp Arg Leu Asp Lys Pro Val Leu Ser Ala Ser Val Ala
                210                 215                 220

Thr Val Tyr Gln Met Leu Lys Ala Leu Gly Leu Lys Ala His Val Ser
225                 230                 235                 240

Asn Ala Gly His Leu Leu Ser Gly Ala Tyr
                245                 250

<210> SEQ ID NO 3
<211> LENGTH: 750
<212> TYPE: DNA
<213> ORGANISM: Pseudomonas fluorescens
<220> FEATURE:
<221> NAME/KEY: CDS
<222> LOCATION: (1)..(750)

<400> SEQUENCE: 3 atg acc aag ccc tac cgt atc ggc cag atc gtg ccg agt tcg aac acc       48
Met Thr Lys Pro Tyr Arg Ile Gly Gln Ile Val Pro Ser Ser Asn Thr
1               5                   10                  15 acc atg gaa acc gag atc ccg gcg atg ctc ctg gcc cgc cag gcg atc       96
Thr Met Glu Thr Glu Ile Pro Ala Met Leu Leu Ala Arg Gln Ala Ile
            20                  25                  30 cgc ccg gag cgc ttc acc ttc cac tcc agc cgc atg cgc atg aag cag      144
Arg Pro Glu Arg Phe Thr Phe His Ser Ser Arg Met Arg Met Lys Gln
        35                  40                  45 gtg aag aag gaa gaa ctg gcg gcg atg gac ggc gag tcc gac cgc tgc      192
Val Lys Lys Glu Glu Leu Ala Ala Met Asp Gly Glu Ser Asp Arg Cys
    50                  55                  60 gca gtg gaa ctg tca gac gcc aag gtg gac gtg ctc ggc tat gcc tgc      240
Ala Val Glu Leu Ser Asp Ala Lys Val Asp Val Leu Gly Tyr Ala Cys
65                  70                  75                  80
```

```
ctg gtg gcg atc atg gcc atg ggg ctg ggg tac cac cgc cag tca gag      288
Leu Val Ala Ile Met Ala Met Gly Leu Gly Tyr His Arg Gln Ser Glu
                85                  90                  95 aag cgg ttg caa aaa gcc act gct gac aac gac gca ctg gcg ccg gtc      336
Lys Arg Leu Gln Lys Ala Thr Ala Asp Asn Asp Ala Leu Ala Pro Val
        100                 105                 110 atc acc agt gcc ggt gcg ctg gtg gaa gcc ctg cac gtg atg aag gcc      384
Ile Thr Ser Ala Gly Ala Leu Val Glu Ala Leu His Val Met Lys Ala
            115                 120                 125 aag cgc atc gcc atc gtc gcg ccc tac atg aag ccg ttg acc gaa ctg      432
Lys Arg Ile Ala Ile Val Ala Pro Tyr Met Lys Pro Leu Thr Glu Leu
130                 135                 140 gtg gtc aac tac atc cgt gag gaa ggc ttc gag gtg cag gac tgg cgc      480
Val Val Asn Tyr Ile Arg Glu Glu Gly Phe Glu Val Gln Asp Trp Arg
145                 150                 155                 160 gcg ctg gaa atc ccc gac aac ctc gcc gtg gcc cgt cac gac acg gcc      528
Ala Leu Glu Ile Pro Asp Asn Leu Ala Val Ala Arg His Asp Thr Ala
                165                 170                 175 aac ctg ccg ggc atc gtc gcc ggc atg aac ctt gag ggc gtc gat gtg      576
Asn Leu Pro Gly Ile Val Ala Gly Met Asn Leu Glu Gly Val Asp Val
            180                 185                 190 gtg gtg ctt tca gcc tgc gtg cag atg cag tcg ctg ccg gca gtc gcc      624
Val Val Leu Ser Ala Cys Val Gln Met Gln Ser Leu Pro Ala Val Ala
        195                 200                 205 aag gtc gag gcg caa acc ggc aaa ccg gtg gtc acc gct gcc atc gcc      672
Lys Val Glu Ala Gln Thr Gly Lys Pro Val Val Thr Ala Ala Ile Ala
    210                 215                 220 acc acc tac gcc atg ctc aag gcg ctg gac ctg gaa ccg gtg gtt ccg      720
Thr Thr Tyr Ala Met Leu Lys Ala Leu Asp Leu Glu Pro Val Val Pro
225                 230                 235                 240 ggc gct ggc gcc ttg ctg tcg ggc gcc tac                              750
Gly Ala Gly Ala Leu Leu Ser Gly Ala Tyr
                245                 250

<210> SEQ ID NO 4
<211> LENGTH: 750
<212> TYPE: DNA
<213> ORGANISM: Citrobacter amalonaticus
<220> FEATURE:
<221> NAME/KEY: CDS
<222> LOCATION: (1)..(750)

<400> SEQUENCE: 4 atg aaa agt ttt cga atc ggc caa atc gtt ccc agc tcc aat act aca       48
Met Lys Ser Phe Arg Ile Gly Gln Ile Val Pro Ser Ser Asn Thr Thr
1               5                   10                  15 atg gag aca gaa ata ccg gcc atg ctt act tct cga tac tcg atg tac       96
Met Glu Thr Glu Ile Pro Ala Met Leu Thr Ser Arg Tyr Ser Met Tyr
                20                  25                  30 cct gac gaa cag ttc aca ttc cac tcc tca cga atg cgc atg atg cat      144
Pro Asp Glu Gln Phe Thr Phe His Ser Ser Arg Met Arg Met Met His
            35                  40                  45 gtt agt cca gag gag ctg aag aaa atg gat att gac agt gat cgt tgt      192
Val Ser Pro Glu Glu Leu Lys Lys Met Asp Ile Asp Ser Asp Arg Cys
        50                  55                  60 gca ctt gag ttg agt gac gct cgc gtt gac gta atg gct tac gcc tgc      240
Ala Leu Glu Leu Ser Asp Ala Arg Val Asp Val Met Ala Tyr Ala Cys
65                  70                  75                  80 ttg gta gcc ata atg tgt cag ggt gcc ggg tat cac aaa gta tct cag      288
Leu Val Ala Ile Met Cys Gln Gly Ala Gly Tyr His Lys Val Ser Gln
```

| | | | | | | | | | | | | |
|---|---|---|---|---|---|---|---|---|---|---|---|---|
| | | | 85 | | | | 90 | | | | 95 | |
| gag | cgc | ttg | ggg | aag | gca | gtg | gct | tct | aat | aat | tca | agc | tct | cca | gtg | 336 |
| Glu | Arg | Leu | Gly | Lys | Ala | Val | Ala | Ser | Asn | Asn | Ser | Ser | Ser | Pro | Val | |
| | | | 100 | | | | | 105 | | | | 110 | | | | |

| ctc | agt | tct | gcg | gga | gcc | ttg | atc | gat | agc | ttg | gcc | atg | ttg | gaa | tac | 384 |
| Leu | Ser | Ser | Ala | Gly | Ala | Leu | Ile | Asp | Ser | Leu | Ala | Met | Leu | Glu | Tyr | |
| | | 115 | | | | | 120 | | | | | 125 | | | | |

| aag | aag | att | tca | atc | atc | acc | ccc | tat | atg | aaa | ccg | ttg | act | cag | caa | 432 |
| Lys | Lys | Ile | Ser | Ile | Ile | Thr | Pro | Tyr | Met | Lys | Pro | Leu | Thr | Gln | Gln | |
| | 130 | | | | | 135 | | | | | 140 | | | | | |

| gtg | atc | gac | tat | att | gag | gca | gca | ggt | atc | gag | gtg | gta | gat | tct | atc | 480 |
| Val | Ile | Asp | Tyr | Ile | Glu | Ala | Ala | Gly | Ile | Glu | Val | Val | Asp | Ser | Ile | |
| 145 | | | | | 150 | | | | | 155 | | | | | 160 | |

| agt | ctc | gaa | gtg | tcg | gac | aac | ctt | gaa | gtt | ggg | cga | ctt | gat | ccg | atg | 528 |
| Ser | Leu | Glu | Val | Ser | Asp | Asn | Leu | Glu | Val | Gly | Arg | Leu | Asp | Pro | Met | |
| | | | 165 | | | | | 170 | | | | | 175 | | | |

| aat | tta | gta | gga | cat | gct | gat | aaa | ctg | aaa | atc | ggt | cag | gct | gat | ggc | 576 |
| Asn | Leu | Val | Gly | His | Ala | Asp | Lys | Leu | Lys | Ile | Gly | Gln | Ala | Asp | Gly | |
| | | 180 | | | | | 185 | | | | | 190 | | | | |

| gtt | gtg | ctt | tcg | tgc | tgc | gtt | caa | atg | ccc | tct | ttg | ccg | gcg | att | cat | 624 |
| Val | Val | Leu | Ser | Cys | Cys | Val | Gln | Met | Pro | Ser | Leu | Pro | Ala | Ile | His | |
| | 195 | | | | | 200 | | | | | 205 | | | | | |

| ctg | gtc | cag | gat | cgc | cta | gac | aaa | ccg | gtt | ctg | tca | gct | tct | gta | gct | 672 |
| Leu | Val | Gln | Asp | Arg | Leu | Asp | Lys | Pro | Val | Leu | Ser | Ala | Ser | Val | Ala | |
| 210 | | | | | 215 | | | | | 220 | | | | | | |

| act | gtc | tac | caa | atg | ttg | aaa | gcc | ctt | ggg | ctg | aag | gcc | cac | gtc | tcg | 720 |
| Thr | Val | Tyr | Gln | Met | Leu | Lys | Ala | Leu | Gly | Leu | Lys | Ala | His | Val | Ser | |
| 225 | | | | | 230 | | | | | 235 | | | | | 240 | |

| aat | gct | ggc | cat | ctc | ctc | tcg | ggc | gct | tac | | | | | | | 750 |
| Asn | Ala | Gly | His | Leu | Leu | Ser | Gly | Ala | Tyr | | | | | | | |
| | | | 245 | | | | | 250 | | | | | | | | |

<210> SEQ ID NO 5
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 5
atgaaaagtt ttcgaatcgg ccaaatcgtt cccagctcc                39

<210> SEQ ID NO 6
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 6
ttagtaagcg cccgagagga gatggcccgg                30

<210> SEQ ID NO 7
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 7
atgaccaagc cctaccgtat cggccagatc gtgc                34

```
<210> SEQ ID NO 8
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 8
tcagtaggcg cccgacagca aggcgcc                                27

<210> SEQ ID NO 9
<211> LENGTH: 21
<212> TYPE: PRT
<213> ORGANISM: Pseudomonas fluorescens

<400> SEQUENCE: 9

Met Thr Lys Pro Tyr Arg Ile Gly Gln Ile Val Pro Ser Ser Asn Thr
1               5                   10                  15

Thr Met Glu Thr Glu
            20

<210> SEQ ID NO 10
<211> LENGTH: 11
<212> TYPE: PRT
<213> ORGANISM: Pseudomonas fluorescens

<400> SEQUENCE: 10

Val Pro Ser Ser Asn Thr Thr Met Glu Thr Glu
1               5                   10

<210> SEQ ID NO 11
<211> LENGTH: 32
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified base
<222> LOCATION: 3
<223> OTHER INFORMATION: i
<220> FEATURE:
<221> NAME/KEY: modified base
<222> LOCATION: 6
<223> OTHER INFORMATION: i
<220> FEATURE:
<221> NAME/KEY: modified base
<222> LOCATION: 12
<223> OTHER INFORMATION: i
<220> FEATURE:
<221> NAME/KEY: modified base
<222> LOCATION: 18
<223> OTHER INFORMATION: i
<220> FEATURE:
<221> NAME/KEY: modified base
<222> LOCATION: 21
<223> OTHER INFORMATION: i
<220> FEATURE:
<221> NAME/KEY: modified base
<222> LOCATION: 30
<223> OTHER INFORMATION: i

<400> SEQUENCE: 11
gtnccnagct cnaacacnac natggaaacn ga                          32

<210> SEQ ID NO 12
<211> LENGTH: 51
<212> TYPE: DNA
<213> ORGANISM: Pseudomonas fluorescens
```

```
<400> SEQUENCE: 12
atgaccaagc ctaccgtatc ggccagatcg tgccgagttc gaacaccacc a            51

<210> SEQ ID NO 13
<211> LENGTH: 20
<212> TYPE: PRT
<213> ORGANISM: Citrobacter amalonaticus

<400> SEQUENCE: 13

Met Lys Ser Phe Arg Ile Gly Gln Ile Val Pro Ser Ser Asn Thr Thr
1               5                   10                  15

Met Glu Thr Glu
            20

<210> SEQ ID NO 14
<211> LENGTH: 60
<212> TYPE: DNA
<213> ORGANISM: Citrobacter amalonaticus

<400> SEQUENCE: 14
atgaaaagtt ttcgaatcgg ccaaatcgtt cccagctcca atactacaat ggagacagaa      60
```